US012569678B2

(12) United States Patent
Wang et al.

(10) Patent No.: US 12,569,678 B2
(45) Date of Patent: Mar. 10, 2026

(54) MULTI-ELECTRODE MINIATURE ELECTRICAL STIMULATION SYSTEM AND TREMOR RELIEF WRISTBAND

(71) Applicants: Fasikl Incorporated, Dallas, TX (US); Hangzhou Fasikl Technology Co., Ltd, Hangzhou (CN)

(72) Inventors: Baitong Wang, Hangzhou (CN); Jules Anh Tuan Nguyen, Dallas, TX (US); Bing Ye, Hangzhou (CN); Linh Hoang, Dallas, TX (US); Markus Drealan, Dallas, TX (US)

(73) Assignees: Fasikl Incorporated, Dallas, TX (US); Hangzhou Fasikl Technology Co., Ltd, Hangzhou (CN)

( * ) Notice: Subject to any disclaimer, the term of this patent is extended or adjusted under 35 U.S.C. 154(b) by 383 days.

(21) Appl. No.: 18/116,334

(22) Filed: Mar. 2, 2023

(65) Prior Publication Data

US 2023/0277841 A1 Sep. 7, 2023

(30) Foreign Application Priority Data

Mar. 7, 2022 (CN) ......................... 202210225130.X

(51) Int. Cl.
*A61N 1/36* (2006.01)
*A61N 1/04* (2006.01)

(52) U.S. Cl.
CPC ....... *A61N 1/36003* (2013.01); *A61N 1/0456* (2013.01); *A61N 1/0484* (2013.01); *A61N 1/36034* (2017.08)

(58) Field of Classification Search
CPC .............. A61N 1/36003; A61N 1/0456; A61N 1/0484; A61N 1/36034; A61N 1/36125; A61N 1/36014
See application file for complete search history.

(56) References Cited

U.S. PATENT DOCUMENTS

| | | | |
|---|---|---|---|
| 2016/0008597 A1* | 1/2016 | Chen | A61N 1/3603 607/60 |
| 2020/0147373 A1* | 5/2020 | Tamaki | A61B 5/1104 |
| 2022/0257174 A1 | 8/2022 | Yildirim et al. | |
| 2022/0273938 A1 | 9/2022 | Chen | |

* cited by examiner

*Primary Examiner* — James M Kish
*Assistant Examiner* — Philip C Edwards

(57) ABSTRACT

The present disclosure discloses a multi-electrode miniature electrical stimulation system, including a BOOST circuit and a voltage doubling circuit; the core of the BOOST circuit is a switching power chip; a stimulation waveform control circuit includes several half-bridge drive circuits; each half-bridge drive circuit is correspondingly connected with one electrode, and any half-bridge drive circuit can output a bidirectional stimulation current; a voltage-controlled constant current source circuit includes an operational amplifier, a multi-channel analog switch and several diffusing power tubes; the operational amplifier works in a negative feedback working state.

9 Claims, 5 Drawing Sheets

MULTI-ELECTRODE MINIATURE ELECTRICAL STIMULATION SYSTEM AND TREMOR RELIEF WRISTBAND

TECHNICAL FIELD

The present disclosure relates to medical wearable nerve stimulation equipment, particularly to a multi-electrode miniature electrical stimulation system and a tremor relief wristband.

BACKGROUND

Electrical energy can be delivered through the skin via electrodes on a skin surface using a nerve stimulation system to stimulate peripheral nerves, as a non-limiting example, such as the median, radialis, and/or ulnar nerves in the upper limbs. It has been shown that the electrical stimulation for these nerves provides therapeutic benefits for various diseases including but not limited to dyskinesia (including but not limited to essential tremor, Parkinson's tremor, postural tremor and multiple sclerosis), urological diseases, gastrointestinal diseases, heart diseases and inflammatory diseases.

Percutaneous electrical nerve stimulation belongs to an electrical stimulation therapy for peripheral nerves. Because of its advantages of no trauma, non-invasiveness, easy operation, good tolerance, short effect, no side effect, low price and the like, the percutaneous electrical nerve stimulation has become a hot spot in clinical application researches, and is widely used, such as various electrical nerve stimulation therapeutic apparatuses based on the percutaneous electrical nerve stimulation.

A wrist-wearable nerve stimulator is small-sized wearable electrical stimulation equipment, which is worn on a wrist. The median nerves, the radialis nerves and/or the ulnar nerves distributed in the hand according to a certain rule through a plurality of electrode sheets clung around the wrist. Generally, an electrical stimulation pulse generation module includes a high-voltage power supply, a stimulation waveform control circuit, a constant current source and other circuit unit modules.

Disadvantages of the Prior Art

Traditionally, the pulse generation module for acupoint stimulation is usually designed on the basis of a transformer pulse generation circuit, which is large in volume, high in power consumption and complicated in structure. At the same time, a pulse current output by the pulse generation module is unstable, which needs to be stabilized by additional configuration of a voltage stabilization module. Therefore, the current electrical stimulation products cannot be miniaturized and can only be used in fixed places. In addition, the electrode sheet for stimulation is usually an adhesive electrode, which is large in volume and cannot be used to stimulate specific acupoints. Moreover, after repeated use, its adhesiveness will be reduced, which will affect the stimulation effect.

The existing electrical stimulation products that can be miniaturized generally realize single-circuit stimulation, a pulse generation module of which usually adopts an open-loop BOOST circuit, so that an output voltage is unstable. Output pulse energy is achieved by adjusting a pulse width of a stimulus waveform, so that a large error is caused, and the stimulation effect and user experience are poor.

SUMMARY

The present disclosure aims to provide a multi-electrode miniature electrical stimulation system and a tremor relief wristband. A high-voltage power supply adopts a BOOST circuit with a feedback function, so that a stable high voltage is output, and the voltage is adjustable. In case of low output stimulation energy, a supply voltage can be lowered to reduce the energy consumption of the system. It is of great significance for using a wearable miniature electrical stimulation product powered by a battery, which can greatly prolong the service life of the product.

In order to achieve the above objective, the technical solution provided in the present disclosure is as follows: a multi-electrode miniature electrical stimulation system is provided, including a main control module and electrodes, wherein the main control module is connected with the electrodes, and the main control module includes:

an adjustable high-voltage circuit module, which includes a BOOST circuit and a voltage doubling circuit, wherein a core of the BOOST circuit is a switching power chip; the voltage doubling circuit is connected behind the BOOST circuit;

a stimulation waveform control circuit, which includes several half-bridge drive circuits, wherein each half-bridge drive circuit is correspondingly connected with one electrode; any half-bridge drive circuit forms a pair and outputs a bidirectional stimulation current; and a voltage-controlled constant current source circuit, which includes an operational amplifier, a multi-channel analog switch and several diffusing power tubes, wherein the operational amplifier works in a negative feedback working state; MCU_DAC_OUT2 is connected with a positive input end of the operational amplifier; an output end of the operational amplifier is connected with the multi-channel analog switch; the diffusing power tubes are connected with the half-bridge drive circuits; and the multi-channel analog switch can make any diffusing power tube connected.

The voltage doubling circuit is connected to an SW end of the switching power chip. The voltage doubling circuit includes three diodes D1, D2 and D3 connected in series, and capacitors C1 and C2; the capacitor C1 is bridged outside the diodes D1 and D2; and the diodes D1 and D2 are grounded after the capacitor C2 is connected between the diodes.

The adjustable high-voltage circuit module further includes a feedback network; an output end of the voltage doubling circuit is also connected with the feedback network; the feedback network includes a resistor R1 and a resistor R6 which are connected in series; and a positive pole of the resistor R6 is connected with pin FB of the switching power chip.

A voltage DA output by the MCU in the main control module is connected to the feedback network through a resistor R5; and the voltage is adjusted by means of adjusting the output voltage DA.

The voltage-controlled constant current source circuit further includes a low-temperature drift sampling circuit connected in series to one of the half-bridge drive circuits and the voltage-controlled constant current source circuit.

The multi-electrode miniature electrical stimulation system further includes an energy storage circuit connected between pin VIN and pin SW of the switching power chip.

The energy storage circuit is an inductor.

The switching power chip adopts TPS61390RGT, and the MCU adopts STM32-series chip.

In order to achieve the above objective, the present disclosure further provides a tremor relief wristband, including a main control module and a wristband body. The wristband body is of a ring structure. The main control module is connected to the wristband body, and is internally provided with a multi-electrode miniature electrical stimulation system.

Compared with the prior art, the multi-electrode miniature electrical stimulation system and the tremor relief wristband of the present disclosure have the beneficial effects:

1. A multi-electrode miniature electrical stimulation pulse generation module is provided, a high-voltage power supply of which adopts a BOOST circuit with a feedback function, so that a stable high voltage is output, and the voltage is adjustable. In case of low output stimulation energy, a supply voltage can be lowered to reduce the energy consumption of the system. It is of great significance for using a wearable miniature electrical stimulation product powered by a battery, which can greatly prolong the service life of the product.

2. A multi-electrode miniature electrical stimulation pulse generation module is provided, an output pulse waveform of which is adjustable. A pulse current is controlled by a constant current source, so that diversification of pulse waveforms can be achieved. The output pulse energy is accurately adjustable and can be applied to occasions sensitive to pulse energy, and the safety of a product is improved.

3. By means of the design of highly miniaturized circuits, a foundation is provided for wearing in the multi-electrode stimulation therapy. The wristband is convenient to carry and can realize treatment at any time.

The present disclosure will become clearer through the following description and in combination with the accompanying drawings. These drawings are used to explain the embodiments of the present disclosure.

DETAILED DESCRIPTION OF THE EMBODIMENTS

Figure 1:
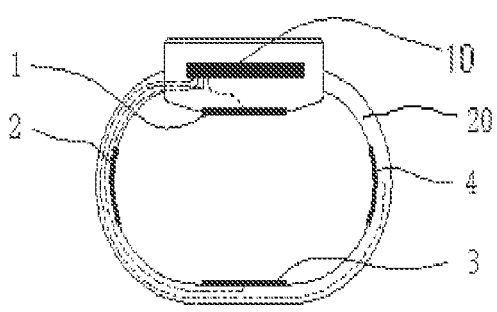
FIG. 1 is a schematic structural diagram of a tremor relief wristband as shown in FIG. 1.

The technical solutions in the embodiments of the present disclosure will be described clearly and completely below in combination with the accompanying drawings of the embodiments of the present disclosure. Apparently, the described embodiments are only part of the embodiments of the present disclosure, not all embodiments.

The components of the embodiments of the present disclosure generally described and shown in the drawings here can be arranged and designed in a variety of different configurations. Therefore, the following detailed description for the embodiments of the present disclosure provided in the accompanying drawings is not intended to limit the scope of the claimed present disclosure, but merely represents selected embodiments of the present disclosure. Based on the embodiments in the present disclosure, all other embodiments obtained by those skilled in the art without creative work shall fall within the scope of protection of the present disclosure.

In the following descriptions, as used in various embodiments of the present disclosure, the terms "including", "having" and their cognates are only intended to indicate specific features, digits, steps, operations, elements, components, or combinations of the foregoing items, and should not be understood as firstly excluding the possibility of the existence of one or more other features, digits, steps, operations, elements, components or combinations of the foregoing items or adding of one or more features, digits, steps, operations, elements, or combinations of the foregoing items.

In addition, the terms "first", "second", "third", etc. are only for the purpose of distinguishing descriptions, and may not be understood as indicating or implying the relative importance.

Unless otherwise defined, all terms (including technical and scientific terms) used herein have the same meanings as commonly understood by those of ordinary skill in the art to which various embodiments of the present disclosure belong. The terms (such as those defined in commonly used dictionaries) will be interpreted as having the same meaning as the contextual meaning in the relevant technical field and will not be interpreted as having idealized or overly formal meanings, unless clearly defined in the various embodiments of the present disclosure.

As mentioned above, referring to FIG. 1, a tremor relief wristband provided in an embodiment of the present disclosure includes a main control module 10 and a wristband body 20. The wristband body 20 is of a ring structure and can be worn on a wrist. The main control module 10 is connected to the wristband body 20. Four electrodes 1, 2, 3, 4 are arranged on an inner side of the wristband body 0. The main control module is internally provided with a multi-electrode miniature electrical stimulation system.

Figure 2:
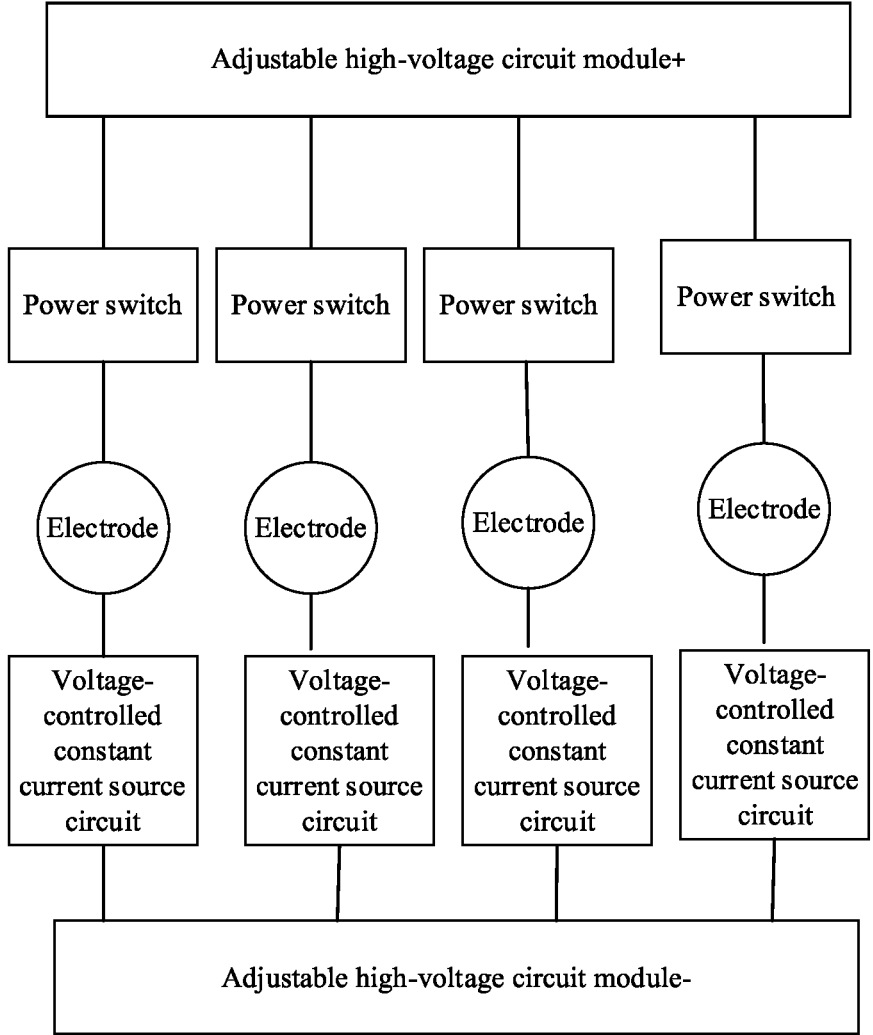
FIG. 2 is a block circuit diagram of a multi-electrode miniature electrical stimulation system of the present disclosure.

As mentioned above, referring to FIG. 2, the multi-electrode miniature electrical stimulation system provided by the embodiment of the present disclosure includes: a main control module 10 and electrodes 1, 2, 3, 4. The main control module 10 is connected with the electrodes 1, 2, 3, 4. The main control module 10 includes an adjustable high-voltage circuit module, multiple power switches, multiple voltage-controlled constant current circuits and multiple electrodes; each power switch can switch on/switch off one of the electrodes, and the electrodes are driven to work by the adjustable high-voltage circuit module and the voltage-controlled constant current circuits.

According to the above, the specific structures and working principles of the adjustable high-voltage circuit module, the multiple power switches and multiple voltage-controlled constant current circuits in the present disclosure and technical effects that can be achieved will be described below in detail in combination with FIG. 3 to FIG. 5.

Figure 3:
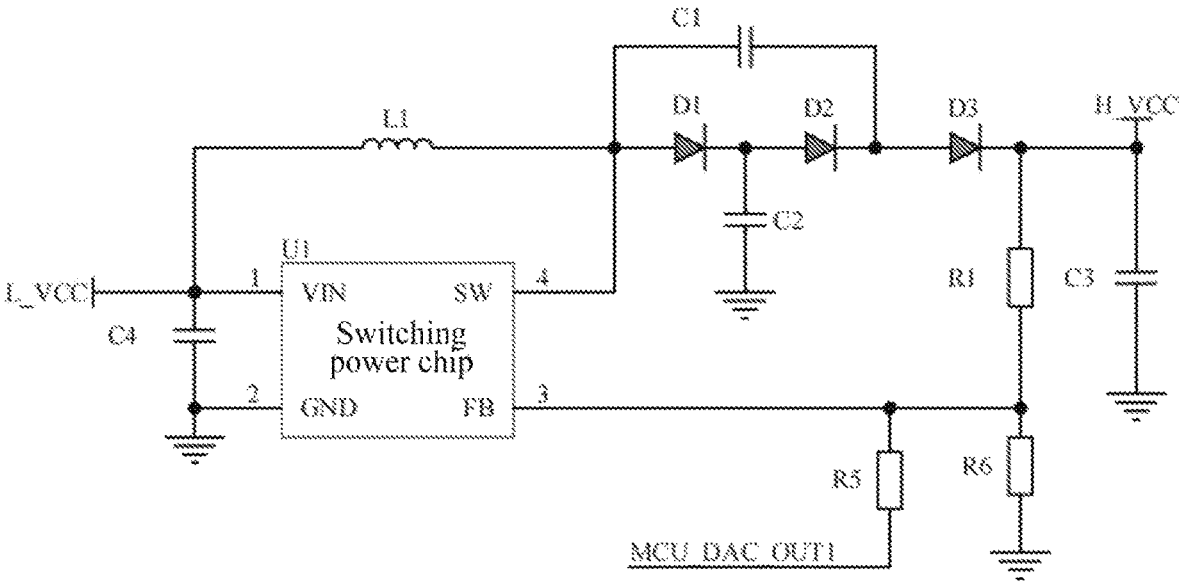
FIG. 3 is a schematic diagram of an adjustable high-voltage circuit module.

Referring to FIG. 3, the adjustable high-voltage circuit module is shown, which includes a BOOST circuit and a voltage doubling circuit. A core of the BOOST circuit is a switching power chip, and the voltage doubling circuit is connected behind the BOOST circuit.

Specifically, referring to FIG. 3, L_VCC is a low-voltage power input, which can be a lithium battery voltage (3.6-4.2 V), that is, a power supply adopted by the present disclosure is a lithium ion battery. C4 is an input capacitor. U1 is a switching power integrated chip. L1 is a boost energy storage inductor. U1 and L1 form the BOOST circuit. D1, D2, D3, C1 and C2 form the voltage doubling circuit.

Specifically, the voltage doubling circuit is connected to an SW end of the switching power chip U1. The voltage doubling circuit includes three diodes D1, D2 and D3 connected in series, and capacitors C1 and C2. The capacitor C1 is bridged outside the diodes D1 and D2; and the diodes D1 and D2 are grounded after the capacitor C2 is connected between the diodes.

Therefore, in the embodiment of the present disclosure, the L_VCC is a low-voltage power input which passes through the BOOST circuit and then further passes through the voltage doubling circuit, and the voltage output by the BOOST circuit is then boosted by the voltage doubling voltage again to generate a high voltage.

Referring to FIG. 3, in one embodiment, the adjustable high-voltage circuit module further includes a feedback network. An output end of the voltage doubling circuit is also connected with the feedback network. The feedback network includes a resistor R1 and a resistor R6 which are connected in series. A positive pole of the resistor R6 is connected with pin FB of the switching power chip.

In one embodiment, a voltage DA output by the MCU in the main control module is connected to the feedback network through a resistor R5, and the voltage is adjusted by means of adjusting the output voltage DA. Therefore, voltage H_VCC of the present disclosure can be flexibly adjusted to adapt to more application scenarios.

Specifically, the voltage output by the BOOST circuit is boosted by the voltage doubling circuit again to generate high voltage H_VCC. The feedback circuit includes the resistor R1 and the resistor R6. R1 and R6 share H_VCC that is input to pin FB of U1 to form the voltage feedback network. MCU_DAC_OUT1 is a DA output pin of a single chip. DA output by the MCU is connected to the feedback network through a resistor R5; and voltage H_VCC can be adjusted by means of adjusting the output voltage DA. U1 may adopt TPS61390RGT, and the MCU may adopt STM32-series chip. The value of L1 may be 4.7 uH. D1, D2, D3 and D4 may adopt BAS521. C4 is 10 uF/10 V; C1 and C2 are 0.1 uF/100 V; and C3 is 0.68 uF/100 V. R1 is 240 K, and R2 and R5 are 3.6 K. Voltage H_VCC is adjustable between 40 V and 80 V.

By means of the adjustable high-voltage circuit module provided by this embodiment, the battery voltage of 3.6 V can be boosted to a high voltage of 80 V. Due to a high step-up ratio, the conventional BOOST circuit is hard to realize. A transformer with a large volume is usually used for boosting, but it cannot be used in occasions with limited volumes and spaces.

Figure 4:
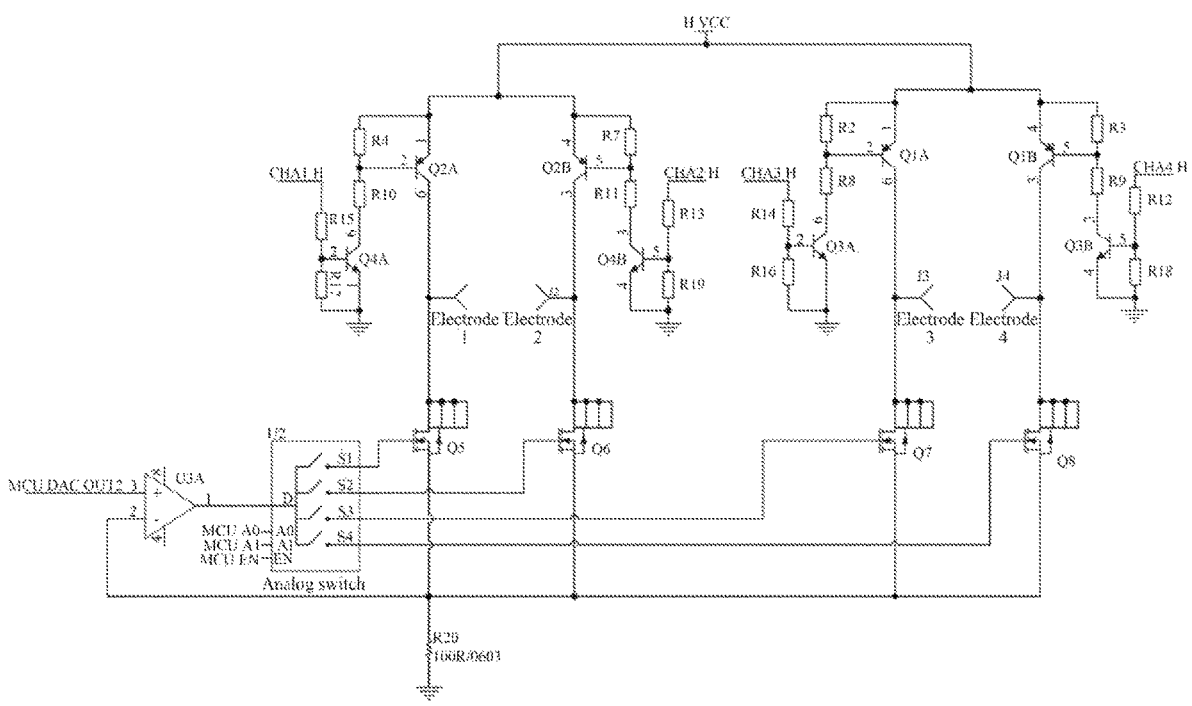
FIG. 4 is a schematic diagram of a stimulation waveform control circuit and a voltage-controlled constant current source.

Referring to FIG. 4, the stimulation waveform control circuit is shown. The stimulation waveform control circuit includes four half-bridge drive circuits. Each half-bridge drive circuit is correspondingly connected with one electrode, and any half-bridge drive circuit can form a pair and output a bidirectional stimulation current.

Specifically, the stimulation waveform control circuit is shown in FIG. 4: Q2A\Q5, Q2B\Q6, Q1A\Q7, and Q1B\Q8 form four half-bridge drive circuits corresponding to electrode 1, electrode 2, electrode 3, and electrode 4 respectively. Among electrodes 1 to 4, any two electrodes can be selected to form one pair to output a bidirectional stimulation current. For example, electrodes 1 and 2 form a pair of electrodes. When tubes Q2A and Q6 are switched on, the current flows from electrode 1 to electrode 2. When tubes Q2B and Q5 are switched on, the current flows from electrode 2 to electrode 1. In this way, the bidirectional stimulation current can be formed.

Specifically, referring to FIG. 4, U3A, U2, Q5 to Q8 and R20 form the voltage-controlled constant current source circuit. MCU_DAC_OUT2 is connected to the DA output pin of the MCU; Q5 to Q8 are diffusing power tubes of the voltage-controlled constant current source; R20 is a low-temperature drift sampling resistor; and U2 is a four-channel analog switch. MCU_A0, MCU_A1 and MCU_EN are connected to an IO port of the MCU; MCU_A0 and MCU_A1 control switching on of S1 to S4 of the analog switch; and MCU_EN controls enabling/disabling of the analog switch.

Referring to FIG. 4, the four half-bridge drive circuits composed of Q2A\Q5, Q2B\Q6, Q1A\Q7 and Q1B\Q8 are also connected with power switches, which are used for driving on and off of upper tubes (triodes) Q2A, Q2B, Q1A, and Q1B in the four half-bridge drive circuits. The power switches are described below:

Specifically, referring to FIG. 4, CHA1_H, CHA2_H, CHA2_H and CHA2_H are connected to the IO port of the MCU to control on and off of Q2A, Q2B, Q1A and Q2B.

More specifically, refer to FIG. 4, CHA1_H is connected to the power switch composed of R15, R17, R4, R10 and Q4A to control on and off of Q2A.

CHA2_H is connected to the power switch composed of R13, R19, R7, R11 and Q4B to control on and off of Q2B.

CHA3_H is connected to the power switch composed of R14, R16, R2, R8 and Q3A to control on and off of Q1A.

CHA4_H is connected to the power switch composed of R12, R18, R3, R9 and Q3B to control on and off of Q1B.

Therefore, each half-bridge drive circuit can drive the power switch through a signal of the MCU to control the on and off of Q2A, Q2B, Q1A and Q1B.

Referring to FIG. 4, the voltage-controlled constant current source circuit includes an operational amplifier U3A, a multi-channel analog switch U2 and four diffusing power tubes Q5, Q6, Q7 and Q8. The operational amplifier U3A works in a negative feedback working state. MCU_DAC_OUT2 is connected with a positive input end of the operational amplifier U3A. An output end of the operational amplifier U3A is connected with the multi-channel analog switch U2. Each of the diffusing power tubes Q5, Q6, Q7 and Q8 is connected with one of the half-bridge drive circuits Q2A, Q2B, Q1A and Q1B. The multi-channel analog switch U2 can make any one of the diffusing power tubes Q5, Q6, Q7 and Q8 connected.

Figure 5:
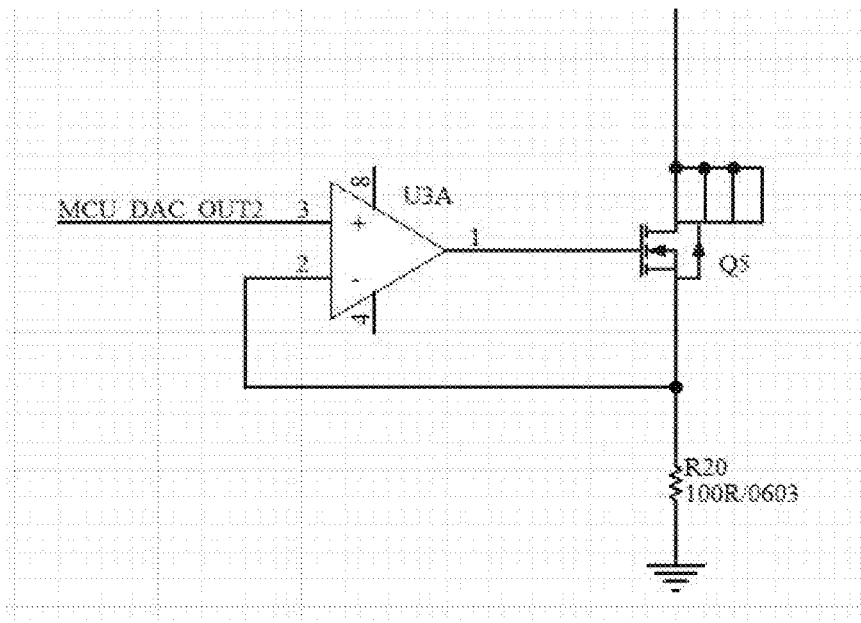
FIG. 5 is a schematic diagram of a voltage-controlled constant current source.

Specifically, referring to FIG. 5, when the analog switch S1 is controlled to be on, the constant current source circuit can be simplified as shown in FIG. 5. The operational amplifier U3A works in the negative feedback working state. A voltage at both ends of the sampling resistor R20 is equal to a voltage output by MCU_DAC_OUT2. A current I on the sampling resistor is equal to VMCU_DAC_OUT2/R20, so that the current I of the sampling resistor can be controlled by means of controlling the voltage output by MCU_DAC_OUT2. The current I of the resistor is a current flowing through Q5.

When electrodes 1 and 2 are selected to form a pair of electrodes, Q2A, Q6 and S2 are switched on, and the current flows from electrode 1 to electrode 2. The current is equal to a current output by the voltage-controlled constant current source, that is, equal to the current on the sampling resistance R20. When Q2B, Q5 and S1 are switched on, the current flows from electrode 2 to electrode 1, and the current is equal to the current of the voltage-controlled constant current source.

When MCU_DAC_OUT2 is an alternating current signal or any other waveform, the stimulation current waveform can output the same waveform.

This circuit features with:

1. The multiple half-bridge circuits can be randomly combined, and the multiple electrodes can be randomly combined.

2. The upper tubes of the half-bridge circuits adopt the triodes which are easily controlled to be on and off and work in on and off states. The lower tubes adopt metal oxide semiconductor (MOS) transistors which work in a linear state. Furthermore, compared with a triode, a MOS transistor does not have a base current that may affect the accuracy of the constant current source.

3. The analog switches are adopted, which can form the constant current source with various MOSs, which reduces the number of devices, reduces the volume and saves the cost.

4. The power voltage H_VCC is adjustable. When the output stimulation current is low, the power voltage H_VCC can be lowered, which reduces heat and saves energy.

5. The stimulation current can be precisely controlled through the output of MCU_DAC_OUT.

6. MCU_DAC_OUT2 can be controlled to output any stimulation waveform.

Only preferred embodiments of the present disclosure are disclosed above. Of course, they are not intended to limit the scope of the claims of the present disclosure. Therefore, equivalent changes made in accordance with the patent scope of the present disclosure still fall within the scope of the present disclosure.

What is claimed is:

1. A multi-electrode miniature electrical stimulation system, comprising a main control module and electrodes, wherein the main control module is connected with the electrodes; the main control module comprises:

a micro control unit (MCU);

an adjustable high-voltage circuit module, which comprises a BOOST circuit and a voltage doubling circuit, wherein a core of the BOOST circuit is a switching power chip; the voltage doubling circuit is connected behind the BOOST circuit;

a stimulation waveform control circuit, which comprises several half-bridge drive circuits, wherein each half-bridge drive circuit is correspondingly connected with one electrode; any half-bridge drive circuit forms a pair and outputs a bidirectional stimulation current; and a voltage-controlled constant current source circuit, which comprises an operational amplifier, a multi-channel analog switch and several diffusing power tubes, wherein digital-to-analog converter output 2 of the MCU (MCU_DAC_OUT2) is connected with the operational amplifier; an output end of the operational amplifier is connected with the multi-channel analog switch; the diffusing power tubes are connected with the half-bridge drive circuits; and the multi-channel analog switch can make any diffusing power tube connected.

2. The multi-electrode miniature electrical stimulation system according to claim 1, wherein the operational amplifier works in a negative feedback working state, and the MCU_DAC_OUT2 is connected with a positive input end of the operational amplifier.

3. The multi-electrode miniature electrical stimulation system according to claim 1, wherein the voltage doubling circuit is connected to a pin Switch (SW) of the switching power chip; the voltage doubling circuit comprises three diodes D1, D2 and D3 connected in series, and capacitors C1 and C2; the capacitor C1 is bridged outside the diodes D1 and D2; and the diodes D1 and D2 are grounded after the capacitor C2 is connected between the diodes.

4. The multi-electrode miniature electrical stimulation system according to claim 1, wherein the adjustable high-voltage circuit module further comprises a feedback network; an output end of the voltage doubling circuit is also connected with the feedback network; the feedback network comprises a resistor R1 and a resistor R6 which are connected in series; and a positive pole of the resistor R6 is connected with a pin Feedback (FB) of the switching power chip.

5. The multi-electrode miniature electrical stimulation system according to claim 4, wherein a voltage DA output by the MCU in the main control module is connected to the feedback network through a resistor R5.

6. The multi-electrode miniature electrical stimulation system according to claim 4, wherein the voltage-controlled constant current source circuit further comprises a low-temperature drift sampling circuit connected in series to one of the half-bridge drive circuits and the voltage-controlled constant current source circuit.

7. The multi-electrode miniature electrical stimulation system according to claim 4, further comprising an energy storage circuit connected between a pin Voltage Input (VIN) and a pin Switch (SW) of the switching power chip.

8. The multi-electrode miniature electrical stimulation system according to claim 7, wherein the energy storage circuit is an inductor.

9. A tremor relief wristband, comprising the multi-electrode miniature electrical stimulation system according to claim 1.

* * * * *